(12) United States Patent
Monath et al.

(10) Patent No.: US 6,878,372 B2
(45) Date of Patent: Apr. 12, 2005

(54) METHODS OF PREVENTING AND TREATING FLAVIVIRUS INFECTION IN ANIMALS

(75) Inventors: Thomas P. Monath, Harvard, MA (US); Juan Arroyo, S. Weymouth, MA (US)

(73) Assignee: Acambis Inc., Cambridge, MA (US)

( * ) Notice: Subject to any disclaimer, the term of this patent is extended or adjusted under 35 U.S.C. 154(b) by 0 days.

(21) Appl. No.: 10/277,478

(22) Filed: Oct. 21, 2002

(65) Prior Publication Data

US 2003/0129201 A1 Jul. 10, 2003

Related U.S. Application Data

(60) Provisional application No. 60/346,845, filed on Oct. 19, 2001.

(51) Int. Cl.$^7$ .................. A61K 39/12; C12N 15/31; C12N 15/33; C12N 15/40
(52) U.S. Cl. ............ 424/93.1; 424/93.2; 424/199.1; 424/218.1; 424/93.6; 435/320.1; 435/5; 435/440.1; 435/235.1
(58) Field of Search ............... 424/93.1, 93.2, 424/93.6, 218.1; 435/320.1, 5, 440, 235.1

(56) References Cited

U.S. PATENT DOCUMENTS 6,184,024 B1 2/2001 Lai et al.

FOREIGN PATENT DOCUMENTS

| WO | WO 93/06214 A1 | 1/1993 |
| WO | WO 98/37911 | 3/1998 |
| WO | WO 01/39802 | 7/2001 |

OTHER PUBLICATIONS

Carle et al. J. bacterialogy 1944, vol. 48, pp. 45–68.*
Davis et al. J. Virol. 2001, vol. 75, No. 9, pp. 440–4047.*
Van Der Most et al. J. Virol. 2000, vol. 74, No. 17, pp. 8094–8101.*
Monath et al. J. Virol. 2000, vol. 74, No. 4, pp. 1742–1751.*

Arroyo et al., "Yellow Fever Vector Live–Virus Vaccines: West Nile Virus Vaccine Development," TRENDS in Molecular Medicine 7:350–354, 2001.

Chambers et al., "Yellow Fever/Japanese Encephalitis Chimeric Viruses: Construction and Biological Properties," J. Virol. 73:3095–3101, 1999.

Chambers et al., U.S. Appl. No. 09/121,587, filed Jul. 23, 1998.

Chambers et al., U.S. Appl. No. 09/452,638, filed Dec. 1, 1999.

Monath et al., "West Nile Virus Vaccine," Current Drug Targets–Infectious Disorders 1:1–14, 2001.

Arroyo et al., "Molecular Basis for Attenuation of Neurovirulence of a Yellow Fever Virus/Japanese Encephalitis Virus Chimera Vaccine (ChimeriVax–JE)," J. Virol. 75:934–942, 2001.

Guirakhoo et al., "Construction, Safety, and Immunogenicity in Nonhuman Primates of a Chimeric Yellow Fever–Dengue Virus Tetravalent Vaccine," J. Virol. 75:7290–7304, 2001.

Guirakhoo et al., "Immunogenicity, Genetic Stability, and Protective Efficacy of a Recombinant, Chimeric Yellow Fever–Japanese Encephalitis Virus (ChimeriVax–JE) as a Live, Attenuated Vaccine Candidate Against Japanese Encephalitis," Virol. 257:363–372, 1999.

* cited by examiner

Primary Examiner—James Housel
Assistant Examiner—Bao Qun Li
(74) Attorney, Agent, or Firm—Clark & Elbing LLP

(57) ABSTRACT

The invention provides methods of preventing and treating flavivirus infection in animals.

9 Claims, No Drawings

US 6,878,372 B2

METHODS OF PREVENTING AND TREATING FLAVIVIRUS INFECTION IN ANIMALS

CROSS-REFERENCE TO RELATED APPLICATIONS

This application claims priority from U.S. Provisional Application Ser. No. 60/346,845, filed Oct. 19, 2001, the contents of which are incorporated herein by reference.

FIELD OF THE INVENTION

This invention relates to methods of preventing and treating flavivirus infection in animals.

BACKGROUND OF THE INVENTION

Flaviviruses are small, enveloped, positive-strand RNA viruses that are of concern in many medical and veterinary settings throughout the world. West Nile (WN) virus, for example, which is a member of the flavivirus family, is the causative agent of WN encephalitis, an infectious, non-contagious, arthropod-borne viral disease (Monath et al., "Flaviviruses," In Virology, Fields (ed.), Raven-Lippincott, New York, 1996, pp. 961–1034). The virus has been found in Africa, western Asia, the Middle East, the Mediterranean region of Europe, and, recently, in the United States. Mosquitoes become infected with the virus after feeding on infected wild birds, and then transmit the virus through bites to humans, birds, and animals, such as horses, sheep, cattle, and pigs.

In 1999, twenty-five horses in New York with neurological symptoms were found to have WN virus infection. These horses presented with signs of ataxia, difficulty walking, knuckling over, head tilt, muscle tremors, and the inability to rise. Of these twenty-five horses, nine died or were euthanized, and virus, as well as virus-specific antibodies, were found in tissue samples from these horses. The sixteen surviving horses all recovered, and also developed WN virus antibody titers. Since then, increasing numbers of West Nile virus-infected horses have been confirmed.

Flavivirus proteins are produced by translation of a single, long open reading frame to generate a polyprotein, which undergoes a complex series of post-translational proteolytic cleavages by a combination of host and viral proteases to generate mature viral proteins (Amberg et al., J. Virol. 73:8083–8094, 1999; Rice, "Flaviviridae," In Virology, Fields (ed.), Raven-Lippincott, New York, 1995, Volume I, p. 937). The virus structural proteins are arranged in the polyprotein in the order C-prM-E, where "C" is capsid, "prM" is a precursor of the viral envelope-bound M (membrane) protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein.

SUMMARY OF THE INVENTION

The invention provides methods of preventing or treating flavivirus infection (e.g., West Nile virus infection) in non-human mammals (e.g., horses), which involve administering to the non-human mammals chimeric flaviviruses. The invention also provides the use of chimeric flaviviruses in the preparation of medicaments for use in such methods. The chimeric flaviviruses can include, for example, the capsid and non-structural proteins of a first flavivirus (e.g., a yellow fever virus, such as a yellow fever virus derived from the 17D strain) and the prM and envelope proteins of a second flavivirus (e.g., West Nile virus).

The invention provides several advantages. For example, as is discussed below, horses treated using the methods of the invention do not present with adverse side effects due to the vaccination, and yet are protected against substantial virus challenge. Thus, the methods of the invention are highly effective at protecting horses against flavivirus, e.g., West Nile virus, infection. In addition, referring specifically to the yellow fever/West Nile virus chimera described herein, the host range of yellow fever virus is very specific, being limited to primates. Thus, the efficacy of the yellow fever/West Nile virus chimera in protecting horses against West Nile virus challenge was surprising, as horses, which are only distantly related to primates, are well outside of the natural host range of yellow fever virus. Further, because the vaccine viruses used in the invention are chimeric, consisting of material from more than one different virus, the chances of reversion to wild type virus are eliminated.

Other features and advantages of the invention will be apparent from the following detailed description and the claims.

DETAILED DESCRIPTION

The invention provides methods of preventing and treating flavivirus (e.g., West Nile (WN) virus) infection in animals, such as horses. The methods of the invention involve vaccination of animals that are at risk of developing or have flavivirus infection with a live, attenuated chimeric flavivirus. These viruses consist of a flavivirus (i.e., a backbone flavivirus) in which a structural protein (or proteins) has been replaced with a corresponding structural protein (or proteins) of a second flavivirus, to which immunity is sought. Preferably, the chimeras consist of a backbone flavivirus in which the prM and E proteins have been replaced with the prM and E proteins of the second flavivirus.

The chimeric viruses that are used in the invention can consist of any combination of viruses, provided that, as is mentioned above, the virus to which immunity is desired is the source of the inserted structural protein(s). For example, to vaccinate an animal, such as a horse, against West Nile virus infection, a chimeric flavivirus consisting of a flavivirus backbone, such as that of yellow fever (YF) virus, into which West Nile virus structural proteins (e.g., prM and E proteins) are inserted can be used. In this chimera, the YF prM and E proteins are replaced with those of WN. Similarly, if immunity against Japanese encephalitis (JE) virus is desired, then the prM and E proteins of JE virus can be inserted into a backbone flavivirus, such as a yellow fever virus, in place of the corresponding backbone proteins. Other flaviviruses that cause disease in horses, and for which chimeric viruses can be used for inducing protection, include Kunjin, Murray Valley encephalitis, and Louping ill viruses.

In addition to horses, animals that can be treated using the methods of the invention include, for example, pigs, sheep, cattle, domestic animals, such as cats and dogs, and domestic birds. As specific examples of non-horse vaccinations, sheep can be treated using a chimeric virus including structural insert proteins from Wesselsbron virus or Louping ill virus, and pigs can be treated using a chimeric virus including structural insert proteins from Japanese encephalitis virus.

Thus, examples of flaviviruses that can be used in the invention, as sources of backbone virus or structural protein inserts, include mosquito-borne flaviviruses, such as Japanese encephalitis, Dengue (serotypes 1–4), Yellow fever, Murray Valley encephalitis, St. Louis encephalitis, West Nile, Kunjin, Rocio encephalitis, Wesselsbron, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the Hepacivirus genus (e.g., Hepatitis C virus). Additional viruses that can be used as the source of inserted structural proteins include viruses from the Pestivirus genus (e.g., Bovine diarrhea virus), and other viruses, such as Lassa, Ebola, and Marburg viruses. As is noted above, preferably, the virus consists of a yellow fever virus backbone containing a West Nile virus insert.

Details of making chimeric viruses that can be used in the invention are provided, for example, in U.S. patent application Ser. Nos. 09/007,664, 09/121,587, and 09/452,638; International applications PCT/US98/03894 and PCT/US00/32821; and Chambers et al., J. Virol. 73:3095–3101, 1999, which are each incorporated by reference herein in their entirety.

The vaccines of the invention can be administered in amounts, and by using methods, which can readily be determined by persons of ordinary skill in this art. The vaccines can be administered and formulated, for example, as a fluid harvested from cell cultures infected with the appropriate chimeric virus. The live, attenuated chimeric virus is formulated as a sterile aqueous solution containing between $10^2$ and $10^8$, e.g., between $10^6$ and $10^7$, infectious units (e.g., plaque-forming units (pfu) or tissue culture infectious doses) in a dose volume of 0.1 to 1.0 ml, to be administered by, for example, subcutaneous, intramuscular, or intradermal routes. In addition, a mucosal route, such as an oral route, may be selected. Selection of an appropriate amount of chimera to administer can be determined by those of skill in this art, and this amount can vary due to numerous factors, e.g., the size, type, and general health of the animal to which the chimera is to be administered.

As is noted above, the vaccines can be administered as primary prophylactic agents to an animal that is at risk of flavivirus infection. The vaccines can also be used as secondary agents for treating flavivirus-infected animals by stimulating an immune response against the infecting flavivirus. Also, although not required, adjuvants can be used to enhance the immunogenicity of the chimeric vaccines. Selection of appropriate adjuvants can readily be carried out by those of skill in this art.

Experimental Results

The safety and efficacy of ChimerVax-WN was evaluated in horses. Efficacy was defined in terms of humoral immune responses and protection from challenge.

Animals

Eleven horses were used in this study, as summarized below in Table 1. The horses were housed in an ABSL3 containment building for the duration of the study, and were fed alfalfa hay and mixed grain.

TABLE 1

Summary of Animal Characteristics and Treatments

| Horse | Sex | Age (years) | Treatment | Comments |
| --- | --- | --- | --- | --- |
| EQ1 | F | 8 | Vaccinated twice | Fully protected from challenge |
| EQ2 | F | 14 | Vaccinated twice | Fully protected from challenge |
| EQ3 | F | 9 | Vaccinated twice | Euthanized before challenge due to laminitis |
| EQ4 | CM | 16 | Vaccinated twice | Fully protected from challenge |
| EQ5 | F | 8 | Challenge model development $10^4$ pfu IT | Euthanized 2 days after challenge; did not develop WN-related disease |
| EQ6 | F | 9 | Challenge model development $10^4$ pfu SC; CSF tap on day 4 | Mild WN-related disease with possible recovery |
| EQ7 | F | 10 | Challenge model development $10^4$ pfu IT | Clinical disease 20–22 days post-inoculation; euthanized on day 24; encephalitis confirmed |
| EQ8 | F | 8 | Challenge model development $10^5$ pfu IT | Severe clinical disease beginning on day 7; encephalitis confirmed |
| EQ9 | CM | 6 | Challenge model development $10^5$ pfu IT | Severe clinical disease beginning on day 8; encephalitis confirmed |
| EQ10 | CM | 8 | Challenge control $10^5$ pfu IT | Severe clinical disease beginning on day 8; encephalitis confirmed |
| EQ11 | CM | 11 | Challenge control $10^5$ pfu IT | Severe clinical disease beginning on day 8; encephalitis confirmed |

Immunization

Four horses (EQ1, EQ2, EQ3, and EQ4) were immunized by two injections, three weeks apart, of ChimeriVax-WN virus. At each immunization, a dose of $10^7$ plaque-forming units (pfu) of virus in 1 ml was inoculated subcutaneously over the left shoulder.

Viremia in the vaccinated horses was analyzed using a standard WN plaque assay. Samples were tested in duplicate, at neat and 1:5 dilution. We found that, although the levels of viremia were very low from day 0 through 7, a peak of viremia was detectable on days 3 and 4.

Antibody levels were measured in samples taken from each horse after vaccination, as is indicated in Table 2, using a plaque reduction neutralization test (PRNT). In summary, two of the horses developed and 80% reduction titer of 10 within two weeks of primary immunization, and all four horses had a titer between 10 and 20 at four weeks (one week following the second immunization).

Validation of an Equine Challenge Model

Mosquito-borne challenge of horses with WNV usually results in viremia, but clinical disease is rare. Thus, to enable assessment of protective immunity to WNV, an appropriate challenge model was developed. The challenge virus used in these studies was WNV NY99 (4132), which was originally isolated from a crow and had been passaged once in Vero cells and once in C636 cells. Due to the hypersensitivity reactions observed following booster vaccine injections, we passaged the virus an additional time in BHK-21 cells, washed the FBS-containing inoculum off after adsorption, and prepared stocks using 20% WNV/SLE-seronegative horse serum. This FBS-free preparation was diluted in PBS and used for the challenges of horses EQ1, EQ2, EQ4, EQ8, EQ9, EQ10, and EQ11.

Most of the horses were challenged by intrathecal inoculation. For this procedure, they were anesthetized with a combination of xylazine and ketamine and a cisternal tap was performed under aseptic conditions. Two ml of CSF were withdrawn, and 1.0 ml of virus was injected. In all cases, recovery from the procedure was uneventful.

The results from challenge development studies are summarized as follows.

Horse EQ5

This horse was inoculated with $10^4$ pfu of WNV by the intrathecal route. The horse appeared normal that day and the following, but was found recumbent and poorly responsive on the morning of day 2. She was euthanized and necropsied, and virus was not recovered from several areas of brain. This animal may have fallen during the previous night and seriously injured her spinal cord, which was not examined at necropsy. It appears clear that her death was not related to WNV infection.

considerably decreased in severity. She was euthanized on day 24 to allow confirmation that the disease was indeed due to WNV. Histopathological examination of brain revealed a diffuse, widespread encephalitis. Serum samples collected twice daily from day 1 to day 9 were assayed for virus by plaqueing on Vero cells; virus was not isolated from any of the samples. We also failed to isolate virus from CSF and from homogenates of cerebrum, cerebellum, and brainstem collected at necropsy (tissues-assayed as 10% suspensions and −1 and −2 dilutions). PRNT titers (80 or 90%) of sera collected on day 0, 7, 14, and 23 were <10, <10, 160, and 160.

Horses EQ8 and EQ9

These horses were challenged by intrathecal inoculation of $10^5$ pfu WNV; back titration revealed the dose administered to be $2 \times 10^5$ pfu. Both animals remained clinically normal for 7 to 7.5 days, then developed progressively severe disease (clinical descriptions on individual animal records). The course of disease in the two horses was almost identical and both were euthanized and necropsied on day 9. Histopathologic examination revealed severe encephalitis in both horses. Sera collected twice daily following inoculation were assayed for plaque production on Vero cells. The viremia titers ($\log_{10}$ pfu/ml) determined were:

|     | Day post-challenge | | | | | | | | | | | | | | | |
| --- | --- | --- | --- | --- | --- | --- | --- | --- | --- | --- | --- | --- | --- | --- | --- |
|     | 0.5 | 1.0 | 1.5 | 2.0 | 2.5 | 3.0 | 3.5 | 4.0 | 4.5 | 5.0 | 5.5 | 6.0 | 6.5 | 7.0 | 7.5 |
| EQ8 | <1 | <1 | <1 | 1.0 | 1.0 | 1.5 | <1 | 1.4 | <1 | <1 | <1 | <1 | <1 | <1 | <1 |
| EQ9 | <1 | <1 | 1.7 | 2.5 | 2.0 | 2.3 | 2.3 | 2.3 | 1.6 | <1 | <1 | <1 | <1 | <1 | <1 |

Horse EQ6

This horse was inoculated with $10^4$ pfu WNV subcutaneously; four days later, a cisternal puncture was performed with the idea of facilitating passage of virus across the blood brain barrier. On the morning of day 10, she was noticeably anxious and not normal, but by that evening, had returned to normalcy. No other clinical signs were observed during the 6 weeks following challenge. Serum samples collected twice daily for the first 13 days after inoculation were assayed for virus on Vero cells—no virus was recovered from any specimen. PRNT assays were performed using serum collected on the day of inoculation and 3 weeks later. The 80% (and 90%) neutralization titers on these samples were 10 (<10) and 40 (40) respectively. She had been tested as serologically negative prior to use, so the 1:10 at 80% titer on the day of inoculation was surprising. This animal may have had a mild case of WN.

Horse EQ7

This horse was inoculated with $10^4$ pfu WNV intrathecally; backtitration of the inoculum revealed the dose to be $6 \times 10^3$ pfu. Clinical signs of disease were absent until day 20, when the animal was noticed to be anxious and nervous. Over the following 2 days, her condition worsened with increased anxiety, head and lip tremors, muscle fasiculation, and rear limb paresis. However, by the evening of day 23, she appeared to be recovering and clinical signs were Samples of CSF, cerebrum, cerebellum, brainstem, and cranial cervical cord collected at necropsy were assayed for virus on Vero cells. EQ8 had a trace (1.5 $\log_{10}$ pfu/gram) of virus in brainstem, and EQ8 had a small amount of virus (1.3 $\log_{10}$ pfu/gram) in cerebellum; all other samples were negative. Both animals had PRNT titers of <10 at the time of challenge. At the time of euthanasia, EQ8 and EQ9 had PRNT titers (90%) of 160 and <10, respectively.

Challenge of Vaccinated Horses and Controls

Vaccinated horses EQ1, EQ2, and EQ4 were challenged exactly 24 weeks after primary immunization. Two additional control horses were challenged simultaneously. All of these challenges consisted of intrathecal inoculation of 1.0 ml containing $10^5$ pfu WVN (FBS-free preparation diluted in PBS). Backtitration of the inoculum indicated that the horses received approximately 125,000 pfu of virus.

The two control horses (EQ10 and EQ11) developed severe clinical disease beginning 7 to 8 days after virus inoculation and were euthanized 8.5 and 10 days after challenge, respectively. At the time of euthanasia, their PRNT antibody titers were 1:40 and <10, respectively. Serum collected at half day intervals between the time of challenge and euthanasia were assayed by plaque production on Vero cells; viremia titers ($\log_{10}$ pfu/ml serum) are shown in the following tables (negative samples from EQ11 taken after day 8.0 not shown).

| | Day post-challenge | | | | | | | | | | | | | | |
|---|---|---|---|---|---|---|---|---|---|---|---|---|---|---|---|
| | 1.0 | 1.5 | 2.0 | 2.5 | 3.0 | 3.5 | 4.0 | 4.5 | 5.0 | 5.5 | 6.0 | 6.5 | 7.0 | 7.5 | 8.0 |
| EQ10 | 1.0 | 1.3 | 1.9 | 1.9 | 2.3 | 2.4 | 2.4 | 1.8 | <1 | <1 | <1 | <1 | <1 | <1 | <1 |
| EQ11 | <1 | 1.0 | 2.8 | 2.9 | 2.5 | 2.4 | 2.4 | 2.3 | | 1.3 | <1 | <1 | <1 | <1 | <1 | <1 |

Samples of CSF, cerebrum, cerebellum, and brainstem collected at necropsy were also assayed by plaque production on Vero cells. Virus was not isolated from either CSF sample. Trace amounts of virus (1–2 plaques per well inoculated with 0.1 ml of 10% suspension) were isolated from all three areas of brain from horse EQ10, and from brainstem only from horse EQ11. Histopathologic examination of the brains of EQ10 and EQ11 revealed widespread encephalitis.

In marked contrast to the two control horses, the vaccinated horses EQ1, EQ2, and EQ4 failed to show any evidence of clinical disease in the 4 weeks following challenge. Further, virus was not isolated from any of the serum samples collected twice daily from these animals during the first 10 days following challenge, nor from samples of cerebrum, cerebellum, brainstem, or CSF collected at necropsy on day 28. Histopathologic examination of their brains did not reveal lesions, other than a few incidental findings not associated with WNV infection.

Antibodies to WNV were assayed in CSF collected at the time of virus inoculation and the time of euthanasia (day 28 for EQ1, EQ2, and EQ4; day 8.5 for EQ10, and day 10 for EQ11). Samples were assayed at dilutions of 1:5, 10, and 20. The samples collected at necropsy from horse EQ1 showed an 87% reduction in plaque count at 1:5, and postmortem sample from EQ4 showed a 98% reduction at 1:5. All other samples had titers of <5 at 80% reduction.

Serological Responses to Vaccination

Serum samples were collected from the four immunized horses weekly for the duration of their tenure and stored in duplicate. Neutralizing antibody titers were determined on a subset of these samples, using a standard plaque-reduction neutralization test on Vero cells. Only some of the assays were conducted using 8% human serum in the virus inoculum, as indicated in Table 2.

TABLE 2

PRNT Results for Horses Immunized with ChimeriVax-WN

| Sample date | Week | Assay Date* | EQ1 80% | EQ1 90% | EQ2 80% | EQ2 90% | EQ3 80% | EQ3 90% | EQ4 80% | EQ4 90% |
|---|---|---|---|---|---|---|---|---|---|---|
| 3/9 | 0 | Several | <10 | <10 | <10 | <10 | <10 | <10 | <10 | <10 |
| 3/16 | 1 | 11/13– | 10 | <10 | <10 | <10 | <10 | <10 | <10 | <10 |
| 3/23 | 2 | 10/27– | 10 | 10 | 10 | 10 | <10 | <10 | <10 | <10 |
| 3/30 | 3 | 10/27– | 10 | <10 | 10 | <10 | <10 | <10 | <10 | <10 |
| 4/6 | 4 | 11/02– | 20 | 10 | 40 | 40 | 10 | 10 | <10 | <10 |
| 4/6 | 4 | 10/27– | 20 | 10 | 20 | 10 | 10 | 10 | 10 | <10 |
| 4/6 | 4 | 11/13– | 20 | 20 | 20 | 10 | 10 | 10 | 10 | 10 |
| 4/13 | 5 | 10/27– | 20 | 20 | 20 | 20 | 10 | <10 | <10 | <10 |
| 5/4 | 8 | 10/27– | 20 | 10 | 10 | <10 | <10 | <10 | <10 | <10 |
| 5/4 | 8 | 11/13– | 20 | 20 | 10 | <10 | <10 | <10 | <10 | <10 |
| 5/18 | 10 | 10/27– | 10 | 10 | 10 | <10 | <10 | <10 | <10 | <10 |
| 6/1 | 12 | 10/27– | 10 | 10 | 20 | 10 | <10 | <10 | <10 | <10 |
| 6/1 | 12 | 11/13– | 20 | <10 | 10 | <10 | <10 | <10 | <10 | <10 |
| 6/29 | 16 | 10/27– | 10 | <10 | 10 | <10 | — | — | <10 | <10 |
| 6/29 | 16 | 11/13– | 10 | <10 | <10 | <10 | — | — | <10 | <10 |
| 7/27 | 20 | 11/13– | 10 | <10 | 10 | <10 | — | — | <10 | <10 |
| 8/24 | 24 | 10/4+ | 20 | 20 | 10 | 10 | — | — | <10 | <10 |
| 8/24 | 24 | 11/02– | 10 | <10 | <10 | <10 | — | — | <10 | <10 |
| 8/24 | 24 | 11/13– | 10 | 10 | <10 | <10 | — | — | <10 | <10 |
| 8/31 | 25 | 10/4+ | 40 | 40 | 20 | 20 | — | — | 20 | 20 |
| 8/31 | 25 | 11/02– | 20 | 10 | 10 | 10 | — | — | 20 | 10 |
| 9/7 | 26 | 10/4+ | ≧320 | ≧320 | ≧320 | ≧320 | — | — | ≧320 | ≧320 |
| 9/7 | 26 | 11/02– | 320 | 160 | 320 | 160 | — | — | 640 | 640 |
| 9/7 | 26 | 11/13– | 320 | 320 | 640 | 320 | — | — | 1280 | 640 |
| 9/14 | 27 | 10/4– | ≧320 | ≧320 | ≧320 | ≧320 | — | — | ≧320 | ≧320 |
| 9/14 | 27 | 11/02– | 160 | 160 | 320 | 320 | — | — | 640 | 320 |
| 9/21 | 28 | 10/4+ | ≧320 | ≧320 | ≧320 | ≧320 | — | — | ≧320 | ≧320 |
| 9/21 | 28 | 11/02– | 160 | 160 | 320 | 320 | — | — | 320 | 160 |
| 9/21 | 28 | 11/13– | 320 | 160 | 320 | 160 | — | — | 640 | 320 |

*indicates with (+) or without (−) use of labile serum factor

What is claimed is:

1. A method of preventing or treating West Nile virus infection in a horse, said method comprising administering to said horse a chimeric flavivirus comprising the capsid and non-structural proteins of a yellow fever virus and the pre-membrane and envelope proteins of a West Nile virus.

2. The method of claim 1, wherein said yellow fever virus is derived from the 17D strain.

3. The method of claim 1, wherein said chimeric flavivirus is administered at a dose ranging between $10^2$ and $10^8$ plaque-forming units (pfu).

4. The method of claim 3, wherein said chimeric flavivirus is administered at a dose ranging between $10^6$ and $10^7$ pfu.

5. The method of claim 1, wherein said horse receives two dosages of said chimeric flavivirus.

6. The method of claim 1, wherein said chimeric flavivirus is administered by a subcutaneous, intramuscular, mucosal, or intradermal route.

7. The method of claim 6, wherein said mucosal route is oral.

8. The method of claim 1, wherein said horse does not have, but is at risk of developing, West Nile virus infection.

9. The method of claim 1, wherein said horse is infected by West Nile virus.

* * * * *

UNITED STATES PATENT AND TRADEMARK OFFICE
CERTIFICATE OF CORRECTION

PATENT NO. : 6,878,372 B2
DATED : April 12, 2005
INVENTOR(S) : Monath el at.

It is certified that error appears in the above-identified patent and that said Letters Patent is hereby corrected as shown below:

Column 3,
Line 9, replace "Hansalova" with -- Hanzalova --.

Column 4,
Line 59, replace "and 80%" with -- an 80% --.

Column 5,
Line 61, replace "fasiculation" with -- fasciculation --.

Column 8,
Line 63, replace "plaque-fomiing" with -- plaque-forming --.

Signed and Sealed this

Twenty-eighth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,878,372 B2  
APPLICATION NO. : 10/277478  
DATED : April 12, 2005  
INVENTOR(S) : Thomas P. Monath and Juan Arroyo Page 1 of 1

It is certified that error appears in the above-identified patent and that said Letters Patent is hereby corrected as shown below:

In the Specification

Col. 1 line 4, please add the following immediately after the title of the application:

STATEMENT AS TO FEDERALLY FUNDED RESEARCH

This invention was made with government support under grant number 5R01AI048297-03 awarded by the National Institute of Allergy and Infectious Diseases (NIAID). The government has certain rights in the invention.

Signed and Sealed this
Twenty-sixth Day of May, 2015

Michelle K. Lee
*Director of the United States Patent and Trademark Office*